United States Patent
Terek

(10) Patent No.: US 6,207,812 B1
(45) Date of Patent: Mar. 27, 2001

(54) CHONDROSARCOMA ASSOCIATED GENES

(75) Inventor: Richard M. Terek, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 09/042,225

(22) Filed: Mar. 13, 1998

(51) Int. Cl.$^7$ .................................................. C07H 21/04
(52) U.S. Cl. ..................... 536/23.1; 536/23.2; 536/23.4; 536/23.5; 536/23.51; 536/23.52; 536/23.53; 536/24.3; 536/24.31; 536/24.32; 536/24.33; 530/350; 530/358
(58) Field of Search ................................. 536/23.1, 23.2, 536/23.4, 23.5, 23.51, 23.52, 23.53, 24.3, 24.31, 24.32, 24.33; 530/350, 358

(56) References Cited

U.S. PATENT DOCUMENTS

| | | |
|---|---|---|
| 4,873,191 | 10/1989 | Wagner et al. . |
| 5,175,384 | 12/1992 | Krimpenfort et al. . |
| 5,175,385 | 12/1992 | Wagner et al. . |

OTHER PUBLICATIONS

Liang et al., "Differential Display of Eukaryotic Messenger RNA by Means of the Plymerase Chain Reaction", Science, vol. 257, Aug. 14, 1992 pp. 967–971.
Gloeckner G. et al., "Genomic Dequence around the CP1 gene", EMBL Database Entry HSAF2996; Accession No. AF002996, May 27, 1997.
Nakanishi T. et al., "Cloning of a mRNA Preferentially Expressed in Chondrocytes by Differential Display . . . ", Biochemical and Biophysical Res. Commun. 234, 206–210 (1997).
Rosier et al., "P–Glycoprotein Expression in Cartilaginous Tumors", Journal of Surgical Oncology 1997; 65:95–105.
Castresana et al., "Amplification of the c–myc Proto–oncogene in Human Chondrosarcoma", Diag. Mol. Path. 1(4):235–38 (1992).
Chen et al., "Intracellular Antibodies as a New Class of Therapeutic Molecules for Gene Therapy", Human Gene Therapy, 5:595–601 (1994).
Clark et al., "Fusion of the EWS Gene to CHN, A Member of the Steroid/Thyroid Receptor Gene Superfamily, in a Human Myxoid Chondrosarcoma", Oncogene, 12(2):229–35 (1996).
Czubayko et al., "Ribozyme–targeting Elucidates a Direct Role of Pleiotrophin in Tumor Growth", J. Biol. Chem., 269(33):21358–63 (1994).
Dobashi et al., "Possible Association of p53 Overexpression and Mutation with High–Grade Chondrosarcoma", Diag. Mol. Path. 2(4):257–63 (1993).
Gerhard, "Fusion of Cells in Suspension and Outgrowth of Hybrids in Conditioned Medium", Plenum Press, pp. 370–71 (1980).

Ghose et al., "Preparation of Antibody–Linked Cytotoxic Agents", Methods in Enzymology, Ch. 20, 93:326–27 (1983).
Gordon, "Transgenic Animals", Intl. Rev. Cytol., 115:171–229 (1989).
Gu et al., "Delection of a DNA Polymerase β Gene Segment in T Cells Using Cell Type–Specific Gene Targeting", Science, 265:103–106 (1994).
Hammer et al., "Production of Transgenic Rabbits, Sheep and Pigs by Microinjection", Nature, 315:680–83 (1985).
Kraemer et al., "Gene Transfer into Pronuclei of Cattle and Sheep Zygotes", Banbury Report 20, Cold Spring Harbor Press, Cold Spring Harbor, NY, pp. 221–227 (1985).
Krimpenfort et al., "Generation of Transgenic Dairy Cattle Using In Vitro Embryo Production", Bio/Technology, 9:844–47 (1991).
Kobayashi et al., "Reversal of Drug Sensitivity in Multi–drug–Resistant Tumor Cells by an MDR1 (PGY1) Ribozyme", Cancer Res., 54:1271–1275 (1994).
Köhler et al., "Continuous Cultures of Fused Cells Secreting Antibody of Predefined Specificity", Nature, 256:495–97 (1975).
Lo, "Transformation by Iontophoretic Microinjection of DNA: Multiple Integrations Without Tandem Insertions", Mol. Cell. Biol., 3:1803–14 (1983).
Mahieu et al., "Construction of a Ribozyme Directed Against Human Interleukin–6 mRNA: Evaluation of Its Catalytic Activity In Vitro and In Vivo", Blood, 84(11):3758–65 (1994).
Palmiter et al., "Transgenic Mice", Cell, 41:343–45 (1985).
Pursel et al., "Genetic Engineering of Livestock", Science, 244:1281–88 (1989).
Reid, "New Developments in the Diagnosis of Chondrosarcoma", J. Pathology, 163:93–94 (1991).
Sullivan, "Development of Ribozymes For Gene Therapy", J. Invest. Derm., 103(5):85s–89s (1994).
Thompson et al., "Germ Line Transmission and Expression of a Corrected HPRT Gene Produced by Gene Targeting in Embryonic Stem Cells", Cell, 56:313–21 (1989).
Van Der Putten et al., "Efficient Insertion of Genes Into the Mouse Germ Line Via Retroviral Vectors", Proc. Natl. Acad. Sci. USA, 82:6148–52 (1985).
Burgess et al, Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue, J of Cell Bio. 111:21, May 1990.*

(List continued on next page.)

Primary Examiner—Julie Burke
(74) Attorney, Agent, or Firm—Ivor R. Elrifi; Ingrid A. Beattie; Mintz, Levin, Cohn, Ferris, Glovsky and Popeo, P.C.

(57) ABSTRACT

The invention features a nucleic acid molecule encoding a chondrosarcoma associated polypeptide and methods for diagnosing patients with chondrosarcoma. the gene.

7 Claims, No Drawings

OTHER PUBLICATIONS

Tao et al., Studies of Aglycosylated Chimeric Mouse–Human IgG, The Journal of Immunology, 143:2595–2601, Oct. 1989.*

Bowie et al, Deciphering the Message in Protein Sequences: Tolerance to Amino Acid Substitutions, Science, 247:1306–1310, Mar. 1990.*

Lazar et al, Transforming Growth Factor alpha: Mutation of Aspartic Acid 47 and Leucine 48 Results in Different Biological Activities, Molecular and Cellular Biology 8 1247–1252, Mar. 1988.*

Gloickner et al, GenBank Accession AF002996, May 27, 1997.*

Ausubel et al, Current Protocols in Molecular Biology, vol. 2, Jan. 1990.*

* cited by examiner

CHONDROSARCOMA ASSOCIATED GENES

BACKGROUND OF THE INVENTION

The invention relates to bone malignancies.

Chondrosarcoma, which usually occurs in late adulthood and old age, is the second most common form of bone malignancy. Conventional chondrosarcoma tumors are graded from stage I through stage III, stage III being the most advanced. In addition to conventional chondrosarcoma, there are other types of chondrosarcoma with distinguishing characteristics: myxoid, mesenchymal, clear cell, and dedifferentiated (spindle cell) chondrosarcoma.

Diagnosis and grading of chondrosarcoma has been problematic. For example, the criteria used to distinguish benign enchondroma from low grade chondrosarcoma include parameters which are difficult to quantify such as increased cellularity and more than occasional binucleate cells. The histologic criteria are not absolute, and the diagnosis is frequently made by taking into account clinical features such as pain, rate of growth, location, and radiologic features. Furthermore, the location of the tumor may affect clinical assessment. For example, lesions in the hand can appear aggressive histologically and yet behave benignly. In contrast, lesions occurring in the pelvis are likely to represent a malignancy despite a relatively innocuous histologic appearance. Notwithstanding attempts to integrate clinicopathologic criteria, it has not been possible to predict which tumors will metastasize or recur.

SUMMARY OF THE INVENTION

The invention is based on the discovery of a novel gene which is differentially expressed in chondrosarcoma cells. Accordingly the invention features an isolated nucleic acid (e.g., genomic DNA, cDNA or synthetic DNA) encoding a chondrosarcoma associated (CSA) polypeptide such as human CSA-1. The term "chondrosarcoma associated" refers to the property of differential expression in chondrosarcoma cell compared to normal cartilage cells. For example, a CSA gene product is expressed at a detectably higher or lower level compared to the level at which it is expressed in normal cartilage cells. A CSA gene product may be expressed solely in chondrosarcoma cells (and not in normal cartilage cells).

The nucleic acid molecule contains a nucleotide sequence encoding a polypeptide having an amino acid sequence that is at least 80% identical to the amino acid sequence of CSA-1 (SEQ ID NO:2). Preferably, the nucleic acid molecule contains the nucleotide sequence of SEQ ID NO:1 or a degenerate variant thereof. For example, the nucleic acid contain the nucleotide sequence of SEQ ID NO:3. The invention also includes a nucleic acid molecule which contains a strand which hybridizes at high stringency to a DNA having the sequence of SEQ ID NO:1, or the complement thereof. A substantially pure DNA having at least 50% sequence identity (preferably at least 70%, more preferably at least 80%, and most preferably at least 90%) to SEQ ID NO:1, and encoding a polypeptide having the differential pattern of expression of a CSA-1 polypeptide is also within the invention. For expression of a CSA polypeptide, a CSA polypeptide encoding nucleic acid molecule is operably linked to regulatory sequences, e.g., a promoter.

The invention also includes a substantially pure CSA polypeptide such as human CSA-1 or a fragment thereof. CSA-1 fragments, e.g., a fragment containing the amino acid sequence of SEQ ID NO: 8), are useful as immunogens for raising anti-CSA antibodies. The CSA polypeptide preferably contains an amino acid sequence that is at least 50% identical to the amino acid sequence of SEQ ID NO:2. More preferably the amino acid sequence of the polypeptide is 75%, 85%, 95%, 98%, and most preferably 100% identical to the amino acid sequence of SEQ ID NO:2. A cell containing a CSA polypeptide-encoding nucleic acid molecule is also within the invention, as is a method of making a CSA polypeptide. Such a method may involve the following steps: (a) providing cell containing a CSA polypeptide-encoding nucleic acid molecule, and (b) culturing it under conditions permitting expression of the nucleic acid molecule.

By "isolated nucleic acid molecule" is meant a nucleic acid molecule that is free of the genes which, in the naturally-occurring genome of the organism, flank a csa gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. The term excludes large segments of genomic DNA, e.g., such as those present in cosmid clones, which contain a gene of interest, e.g., a csa gene, flanked by one or more other genes which naturally flank it in a naturally-occurring genome.

Nucleic acid molecules include both RNA and DNA, including cDNA, genomic DNA, and synthetic (e.g., chemically synthesized) DNA. Where single-stranded, the nucleic acid molecule may be a sense strand or an antisense strand. The term therefore includes, for example, a recombinant DNA which is incorporated into a vector, into an autonomously replicating plasmid or virus, or into the genomic DNA of a prokaryote or eukaryote at a site other than its natural site; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence.

Hybridization is carried out using standard techniques such as those described in Ausubel et al., *Current Protocols in Molecular Biology,* John Wiley & Sons, (1989). "High stringency" refers to DNA hybridization and wash conditions characterized by high temperature and low salt concentration, e.g., wash conditions of 65° C. at a salt concentration of approximately 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at about 42° C., and about 50% formamide; a first wash at about 65° C., about 2× SSC, and 1% SDS; followed by a second wash at about 65° C. and about 0.1% ×SSC. Lower stringency conditions suitable for detecting DNA sequences having about 50% sequence identity to csa-1 gene are detected by, for example, hybridization at about 42° C. in the absence of formamide; a first wash at about 42° C., about 6× SSC, and about 1% SDS; and a second wash at about 50° C., about 6× SSC, and about 1% SDS.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria. The same rule applies for nucleic acid molecules.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably 100 nucleotides or 300 nucleotides.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

By "promoter" is meant a minimal DNA sequence sufficient to direct transcription. Promoters may be constitutive or inducible, and may be coupled to other regulatory sequences or "elements" which render promoter-dependent gene expression cell-type specific, tissue-specific or inducible by external signals or agents; such elements may be located in the 5' or 3' region of the native gene, or within an intron. DNA encoding a CSA polypeptide may be operably linked to such regulatory sequences for expression of the polypeptide in prokaryotic or eukaryotic cells. By "operably linked" is meant that a coding sequence and a regulatory sequence(s) are connected in such a way as to permit gene expression when the appropriate molecules (e.g., transcriptional activator proteins) are bound to the regulatory sequence(s).

A protein is substantially free of naturally associated components when it is separated from those contaminants which accompany it in its natural state. (proteins and other naturally-occurring organic molecules) which naturally accompany it. Typically, the polypeptide is substantially pure when it constitutes at least 60%, by weight, of the protein in the preparation. Preferably, the protein in the preparation is at least 75%, more preferably at least 90%, and most preferably at least 99%, by weight, CSA-1 polypeptide. A substantially pure CSA-1 polypeptide may be obtained, for example, by extraction from a natural source (e.g., a chondrosarcoma cell); by expression of a recombinant nucleic acid encoding an CSA-1 polypeptide; or by chemically synthesizing the protein. Purity can be measured by any appropriate method, e.g., column chromatography, polyacrylamide gel electrophoresis, or HPLC analysis. Accordingly, substantially pure polypeptides include recombinant polypeptides derived from a eukaryote but produced in *E. coli* or another prokaryote, or in a eukaryote other than that from which the polypeptide was originally derived.

The invention also features CSA polypeptide binding species, such as an antibody or antibody fragment which specifically binds to a CSA polypeptide, e.g., a CSA-1-specific antibody. Antibodies specific for a CSA polypeptide are useful to diagnose chondrosarcoma.

Chondrosarcoma is diagnosed by measuring expression of csa gene expression in patient tissue samples. Expression of CSA-1 is detectable in chondrosarcoma cells but not in normal cells (or in certain other types of tumors which were tested). Thus, the use of CSA polypeptides and CSA polypeptide-encoding nucleic acid molecules in diagnosing and grading of chondrosarcoma is also within the invention. For example, a method for diagnosing the presence of a chondrosarcoma cell in a tissue sample is carried out by measuring expression of a csa gene, e.g., a gene encoding CSA-1, in the tissue sample and a control sample such as a normal nonneoplastic cartilage cell. An increase in expression of the csa gene in the tissue sample compared to the control sample indicates that the tissue sample contains a chondrosarcoma cell. A method of grading a chondrosarcoma tumor may be carried out by determining the level of csa-1 gene expression in a test sample and comparing it to the level of csa-1 gene expression in a control sample. The level of expression in the test sample compared to the control sample is directly proportional to the grade or stage of tumor, i.e., the greater the level of expression of a csa gene the more advanced the stage of the tumor.

In addition to evaluating tissue biopsy samples for csa gene expression, csa gene expression may be detected in vivo. For example, a diagnostically effective amount of a detectably labeled CSA-1-specific binding species may be administered to a patient, followed by a determination of whether the species specifically binds to cartilage cells of the patient. Binding of the CSA-1 binding species, e.g., a CSA-1-specific antibody, antibody fragment, or non-antibody CSA-1 binding compound, to patient cells is an indication of the presence of chondrosarcoma in the patient. The level of binding correlates with the grade of the chondrosarcoma, i.e., a greater amount of binding compared to a normal control of known low grade tumor indicates that the patient's tumor is of a high grade. Similarly, a method of detecting progressive chondrosarcoma in a patient may be carried out as follows: (a) successively administering to a patient suspected of having a chondrosarcoma a diagnostically effective amount of a detectably labeled CSA-1-specific binding species (e.g., an antibody labelled with a radioisotope or a paramagnetic label), and (b) comparing the amount of the species that binds to cartilage cells of the patient in each successive administration to detect an increase of binding of the binding species over time. An increase in binding over time is an indication of progressive chondrosarcoma in said patient. Where the detecting step is quantitative, the amount of binding would correlate with and allow diagnosis of the severity of the disease. A diagnostic method carried out multiple times by repeatedly administering at spaced intervals the labelled binding species to the patient, with the administrations spaced by, e.g., a day, a week, a month, several months, or even years, is a useful method for detecting progression of disease in a patient.

Compounds capable of inhibiting expression of a CSA polypeptide may be therapeutically useful to treat chondrosarcoma. Accordingly, the invention includes a compound capable of inhibiting expression of a CSA polypeptide, e.g., CSA-1, by (a) providing a chondrosarcoma cell expressing a CSA polypeptide, (b) contacting the cell with the candidate compound, and (c) determining the amount of expression of the CSA polypeptide by the cell. A decrease in the amount of CSA polypeptide expression in the presence of the candidate compound compared to that in the absence of the candidate compound indicates that the compound inhibits expression of the CSA polypeptide.

The invention also includes a method of inhibiting the expression or activity of CSA-1. Suitable antagonists include a nucleic acid molecule that interfere with transcription or translation of csa-1, for example, antisense nucleic acid molecules and ribozymes. Also included are antibodies or other suitable antagonistic molecules, that specifically binds CSA-1 polypeptide and "neutralize" its activity.

In addition to diagnostic methods, such as described above, the present invention encompasses methods and compositions for evaluating appropriate treatment, and treatment effectiveness of malignancies associated with expression of csa-1. For example, the csa-1 can be used as a probe to classify cells in terms of their level of csa-1 expression, or as primers for diagnostic PCR analysis in which mutations and allelic variation of csa-1 can be detected.

The invention also includes non-human transgenic animals that express human CSA-1 and non-human transgenic mammal with a null mutation in its endogenous CSA-1 gene. These animals can serve as new and useful models of chondrosarcoma. The invention also includes a transgenic non-human mammal, e.g., a rodent such as a mouse, the germ cells and somatic cells of which contain a null mutation, e.g., a deletion, in DNA encoding a csa gene. By "null mutation" is meant an alteration in the nucleotide sequence that renders the gene incapable of expressing a functional protein product. The mutation could be in csa gene regulatory regions or in the coding sequence. It can, e.g., introduce a stop codon that results in production of a truncated, inactive gene product or it can be a deletion of all or a substantial portion of the coding sequence.

The invention also features an isolated nucleic acid (e.g., genomic DNA, cDNA or synthetic DNA) encoding a cartilage associated (CAA) polypeptide such as human CAA-1. The term "cartilage associated" refers to the property of differential expression in cells of the cartilage lineage compared to cells of other tissue specificities. For example, a CAA gene product is expressed in normal cartilage cells and chondrosarcoma cells but not cells of other tissue specificities or other tumor types.

The nucleic acid molecule contains a nucleotide sequence encoding a polypeptide having an amino acid sequence that is at least 80% identical to the amino acid sequence of CAA-1 (SEQ ID NO:7). Preferably, the nucleic acid molecule contains the nucleotide sequence of SEQ ID NO:6 or a degenerate variant thereof. For example, the nucleic acid may have the nucleotide sequence of SEQ ID NO:5. The invention also includes a nucleic acid molecule which contains a strand which hybridizes at high stringency to a DNA having the sequence of SEQ ID NO:6, or the complement thereof. A substantially pure DNA having at least 50% sequence identity (preferably at least 70%, more preferably at least 80%, and most preferably at least 90%) to SEQ ID NO:7, and encoding a polypeptide having the activity of CAA-1. By the activity of CAA-1 is meant inhibition of interferon gamma induced upregulation of HLA class II antigens. For expression of a CAA polypeptide, a CAA polypeptide encoding nucleic acid molecule is operably linked to regulatory sequences, e.g., a promoter.

The invention also includes a substantially pure CAA polypeptide such as human CAA-1 or a fragment thereof. The CAA-1 polypeptide preferably contains an amino acid sequence that is at least 50% identical to the amino acid sequence of SEQ ID NO:7. More preferably the amino acid sequence of the polypeptide is 75%, 85%, 95%, 98%, and most preferably 100% identical to the amino acid sequence of SEQ ID NO:7. A cell containing a CAA polypeptide-encoding nucleic acid molecule is also within the invention, as is a method of making a CAA polypeptide. Such a method may involve the following steps: (a) providing cell containing a CAA polypeptide-encoding nucleic acid molecule, and (b) culturing it under conditions permitting expression of the nucleic acid molecule.

The invention also features CAA polypeptide binding species, such as an antibody or antibody fragment which specifically binds to a CAA polypeptide, e.g., a CAA-1-specific antibody. Antibodies specific for a CAA polypeptide are useful to for tissue typing and for therapeutic applications, e.g., to inhibit the activity of CAA-1.

Compounds capable of inhibiting expression of a CAA polypeptide may be therapeutically useful to treat conditions, e.g., rheumatoid arthritis, associated with undesired or pathologic joint inflammation. Accordingly, the invention includes a method of screening a candidate compound to identify a compound capable of inhibiting expression of a CAA polypeptide, e.g., CAA-1, by (a) providing a cell expressing a CAA polypeptide, (b) contacting the cell with the candidate compound, and (c) determining the amount of expression of the CAA polypeptide by the cell. A decrease in the amount of CAA polypeptide expression in the presence of the candidate compound compared to that in the absence of the candidate compound indicates that the compound inhibits expression of the CAA polypeptide. A method of identifying a compound which inhibits the activity of CAA-1 can be carried out as follows: (a) providing a cell expressing a CAA polypeptide, (b) contacting the cell with the candidate compound, and (c) determining the amount of HLA II expression by the cell. A decrease in the amount of HLA II expression in the presence of the candidate compound compared to that in the absence of the candidate compound indicates that the compound inhibits HLA II expression in the cell.

Methods of treating undesired inflammation such as that associated with rheumatoid arthritis and other inflammatory arthropathies are also within the invention. Such a method may be carried out by administering to a mammal in need of such therapy, e.g. a patient suffering from rheumatoid arthritis or other inflammatory arthropathies, an effective amount of a CAA-1 polypeptide. For example, the peptide is administered locally at the site of a rheumatoid lesion to reduce local inflammation and swelling.

The invention also includes a non-human transgenic mammal that expresses human CAA-1 and non-human transgenic mammal with a null mutation in its endogenous CAA-1 gene.

Other features and advantages of the invention will be apparent from the following description of the preferred embodiments thereof, and from the claims.

DETAILED DESCRIPTION

To date, no consistent genetic abnormality has been associated with chondrosarcoma. The tumors are heterogeneous and often have a number of abnormalities in gene expression. The following examples provide evidence of a novel gene, csa-1, that is expressed in a human chondrosarcoma cell line and in cartilaginous neoplasms but not in normal cartilage. The level of expression of a CSA-1 polypeptide correlates with the histological grade of the neoplasm, i.e., an increase in expression indicates a higher grade tumor. Detection of a CSA-1 gene product or csa-1 transcript is a means by which to distinguish a neoplastic cell from a normal cartilage cell.

CSA polypeptides and CAA polypeptides may be used therapeutically. For example, a CAA polypeptide such as CAA-1 may function as a tumor suppressor. CAA-1 can also be administered to patients to reduce undesired inflammation such as joint inflammation in rheumatoid arthritis.

CSA-1 plays a role in potentiating chondrogenesis associated with chondrosarcoma. Transfecting the nonexpressing or normal cell lines with vectors which promote high levels of expression of a CSA polypeptide, e.g., CSA-1, followed by transformation of a low grade cell line to a high grade cell line indicates that CSA expression potentiates neoplastic growth. Inhibitors of CSA-1 expression can slow or inhibit neoplastic growth. Transformation and grading of transformed cells is evaluated by examining changes in morphology, proliferation, adhesion, and invasiveness.

Two novel genes have been cloned. CSA-1 is expressed in a tumor cell line and also in some high grade chondrosarcoma, but not normal cartilage, or low, or intermediate grade tumors. A second gene, CAA-1, is expressed in normal cartilage and an intermediate grade tumor cell line, and as alternative sized messages in a high grade cell line.

EXAMPLE 1

Cloning of csa Genes

Chondrosarcoma cell lines derived from human grade I, II and III chondrosarcomas were alternately cultured in monolayer cultures and in agarose suspension cultures using standard methods. Total cellular RNA was isolated using standard techniques. Three different human chondrosarcoma cell lines (AQ, stage II tumor; FS, stage II tumor; and MW, stage I tumor) and normal articular cartilage obtained from amputation specimens was analyzed.

Using the differential mRNA display technique, a technique that systematically amplifies mRNAs by means of RT-PCR with different sets of 5' arbitrary primers and 3' oligo-dT anchoring primers, the mRNA patterns of different cells and cell types were compared. The PCR products were resolved on a denaturing polyacrylamide sequencing gel to display mRNA patterns that distinguish one cell type from another. The bands that were separated by gel electrophoresis represent the 3'-termini of the cDNAs. Therefore, a band that is present in one cell type, e.g., a chondrosarcoma cell line or chondrosarcoma biopsy tissue, but not in the normal cartilage tissue or in noncartilage tissue, suggests that the gene is differentially expressed in chondrosarcomas.

cDNA was generated using reverse transcriptase and an oligo-dT primer (TTTTTTTTTTTTMN (SEQ ID NO:4), where M can be C, G, or A; N can be C, G, A, or T). A PCR reaction was then carried out in triplicate with the same oligo-dT primer and a second random ten base pair primer (RNAmap, GenHunter Corp., Brookline, Mass.). This combination of primers amplified approximately 100 cDNAs from 100–500 base pairs long. The cDNAs were separated on a sequencing gel. A band that is present in one or more of the cancer cell lines and absent in a normal cell may represent an oncogene which is being expressed in the cancer cell but not the normal cell. Conversely, a band that is absent in one or more of the cancer cell lines and present in a normal cell may represent a tumor suppressor gene which is not being expressed because of a mutation or regulatory defect.

The cDNA of a differentially expressed mRNA was eluted from the sequencing gel and reamplified in a PCR reaction with the same primers as was used in the differential display reaction and cloned into a pCR™ II vector (Invitrogen, San Diego, Calif.). Specific mRNAs that were present solely in chondrosarcoma cells were identified and the corresponding cDNAs cloned. cDNAs were sequenced using the M13 forward and reverse sequencing primers, which flank the cloning site of the pCR™ vector. Some sequences were identical to known genes, e.g., cyclin D2, a cell cycle regulatory protein, and PTX3, a member of the pentaxin gene family. Novel cDNAs, i.e., those without sequence similarity to known genes, were used for Northern blotting to confirm that the corresponding gene is differentially expressed in chondrosarcoma cells. Twenty such cDNA probes were used to screen for differential expression of mRNA and sequenced (TABLE 1). A novel gene, csa-1, was found to be differentially expressed in chondrosarcoma cells compared to normal cartilage cells and other cell types such as breast, lung, and colon cells.

TABLE 1

| Clone | Gel Type | MW(I) | FS(II) | AQ(III) | NI Cart |
|-------|----------|-------|--------|---------|---------|
| FS1   | DD       | −     | +      | −       | −       |
|       | N3-0     | −     | +      | +       | −       |
|       | N3-1     | −     | +      | +       | +       |
| FS2   | DD       | −     | +      | −       | −       |
| E1    | DD       | −     | −      | −       | +       |
|       | N3-2     | −     | +      | +       | +       |
|       | N3-3     | −     | +      | +       | −       |
| FS3   | DD       | +     | +      | +       | −       |
| AQ1   | DD       | −     | −      | +       | −       |
| E2    | DD       | −     | −      | −       | +       |
| AQ3   | DD       | −     | −      | +       | −       |
| E6    | DD       | −     | −      | −       | +       |
| AQ2   | DD       | −     | −      | +       | −       |
| E7    | DD       | −     | −      | −       | +       |
| FS10  | DD       | +     | +      | +       | −       |
| FS11  | DD       | +     | +      | +       | −       |
| AQ6   | DD       | −     | −      | +       | +       |
| FS8   | DD       | +     | +      | −       | +       |
| MW1   | DD       | +     | −      | −       | −       |
| MW2   | DD       | +     | −      | −       | −       |
| MW3   | DD       | +     | −      | −       | −       |
| FS9   | DD       | −     | +      | +       | +       |
| FS10  | DD       | −     | +      | −       | −       |
| AQ5   | DD       | −     | +      | +       | +       |

DD: Differential Display Gel
N: Northern Blot

Cloning of csa-1

The gene encoding CSA-1 was identified using differential display PCR as described above. FS8 is a probe corresponding to one of the differentially expressed sequences identified. As shown in TABLE 1, the differential display gel from which probe FS8 was isolated indicated that this gene was not expressed in the AQ cell line. In a Northern blot assay, the probe hybridized to a message approximately 0.85 kb in size in the FS cell line as well as in a high grade chondrosarcoma. No message was detected in normal cartilage, bovine growth plate, or grade 1 or 2 chondrosarcoma.

The FS8 probe (specific for CSA-1) which corresponded to the 3' end of the csa-1 gene was found to be 250 bases long. 5' Rapid Amplification of cDNA (5' RACE) was used to clone the full length gene. A gene specific primer was synthesized which is complementary to the probe was made and used as a primer to synthesize cDNA using RNA from the FS cell line as a template. The RNA was digested away with Rnase H, and an anchor primer was added to the 3' end with TdT and dCTP. PCR was performed using the 3' anchor primer and a second, nested gene specific primer, thereby yielding double stranded DNA which is an extension of the gene fragment from which the differential display probe was derived. The 5'RACE generated fragment was cloned and sequenced.

Expression of CSA-1 in chondrosarcoma cells was localized to the nucleus of the cells by immunostaining using a rabbit polyclonal antibody specific for a CSA-1 polypeptide.

The sequence of the full length csa-1 cDNA (TABLE 2) was found to have an open reading frame (ORF) (TABLE 3 and shown in bold in TABLE 2) encoding a fifty-two amino acid gene product, CSA-1 (TABLE 4).

corresponding to one of the differentially expressed sequences identified. As shown in TABLE 1, E1 was expressed in normal cartilage, but not in any of the human chondrosarcoma cell lines tested by differential display PCR. A northern blot with probe E1 showed expression of a 2.2 kb message in normal articular cartilage and the FS cell line. In contrast, 2 alternative sized transcripts (7.5 kb and 1.2 kb) were detected in the high grade cell line AQ. These data indicate that the caa-1 gene may be alternatively spliced or rearranged in the AQ cell line. The pattern of expression indicates that CAA-1 functions as a tumor suppressor gene.

Expression of CAA-1 expression was analyzed using Northern blotting and RT-PCR in human chondrosarcoma cell lines osteoblasts, normal cartilage, muscle, primary chondrosarcoma and a panel of tumors and normal tissues.

TABLE 2

CSA-1 cDNA

ACTTCCCTGGGTTCACAGCAGGGGTGGAACTGGATTCTTCCTGGATGGGGATCCAGATGG (SEQ ID NO:3)

AGGTGGAGCTGCACCCCTTGTAGAGAATGGCTGCGGGTCCCAGGCCAGGAGCTCCCTGCA

GGGCGGGGGCTCCCACGATCGTATTGACCTCTGGAAGAAGACAGACACTTTCCCACGGGA

GCTCCTCTCCAGCCAGAGCTACACTTGGCAAACCTTTGGTCCTAAATGATTATTCACTGA

ATTGAAGAAATACGGTTTACATATCTTCCAAGTATATATGTAGGGTTGATTTGGGAAGCA

GAACACAGCAGCCCAAATTTGCTTGTAATGTCTGCGACTACAGCCTGCTGGCCTGCCTTC

ACTGTCTTGGGGGAAGCTCGGGGAGACCAGGTGGACTGGAGTAGACTGTGCAGAGACACT

GGTCTGGTGAAGATGTCCAGGAAACCACGAGCCTCCAGCCCATTTTCCAACAACCACCCA

TCAACACCAAAGAGGTTCCCAAGACAACCCAGAAGGGAAAAGGGACCCGTCAAGGAAGTT

CCAGGAACAAAAGGCTCTCCCTAAAAGACCACCGCTTCAAAAAAACCTGAGGAATGGAGT

GGGCCAACACTATCCAGCCACTCTGACCAGCCGAACGAGGAACTCAATCAAAATGCGCCA

TAGCAGGACCACAAGGGCAAGGAGACCACCGCCTTCTCCAGTGCTTCCTTGGGCAGCCAG

TAATTCCCAGGCAAGGCCAGAGACTTCAAGTCTATCTGAAAAGTCTCCAGAAGTCTAACC

CCAGATAAATAGCCAACAGGGTGTAGAGTACGTTTTACACCCAAAGGGTAATGCCCCATG

GTGATGGAAATAAAATGAACATGTTGTAAATGAAAAAAAAAAA

TABLE 3

CSA-1 coding sequence

ATGGCTGCGGGTCCCAGGCCAGGAGCTCCCTGCAGGGCGGGGGCTCCCACGATCGTATTG (SEQ ID NO:1)

ACCTCTGGAAGAAGACAGACACTTTCCCACGGGAGCTCCTCTCCAGCCAGAGCTACACTT

GGCAAACCTTTGGTCCTAAATGATTATTCACTGAATTGAAGAAA

TABLE 4

CSA-1 AMINO ACID SEQUENCE

MAAGPRPGAPCRAGAPTIVLTSGRRQTLSHGSSSPARATLGKPLVLNDYSLN (SEQ ID NO:2)

Cloning of caa-1

The gene encoding CAA-1 was also identified using differential display PCR as described above. E1 is a probe Northern blotting was performed with E1 and with a 1.5 kb 5' RACE generated portion of the gene as probes. PCR was performed using primers which amplify 306 bp of the caa gene.

Differential display of mRNA showed expression of a gene in normal cartilage and in the FS and AQ cell lines (but not in the MW cell line). The differential display probe (E1) was sequenced, found to be novel, and used for Northern blot analysis, which revealed an estimated message size of 2.2 kb in normal cartilage and FS, but not MW, osteoblast, muscle or bovine growth plate.

5' RACE was performed using oligonucleotide primers complementary to the 5' end of clone E1 and yielded a 1.5 kb fragment. In order to obtain the remaining 5' portion of the gene, 5' RACE was repeated with new 5' primers and an additional 0.5 kb fragment was cloned, and the overlapping gene fragments were sequenced.

Northern blotting was performed with the 1.5 kb fragment and a 2.0 kb message was detected in four different samples of FS RNA and in a grade II chondrosarcoma (CS) and FS RNA. The full length gene is 1955 nucleotides in length, which correlates with the message size seen with Northern blotting.

TABLE 5

CAA-1 cDNA

| |
|---|
| CACGCAAAGCAGTGTGGGTTGATTCTGAGGTGCACTGTGGGAAAGAGCTTGTCGCTGCGG (SEQ ID NO:5) |
| TGTTGCTGTTGGAGACTCGATTGTTGGTGACAGCGAAAGAACGATAACAAAATGCCGGAG |
| CGAGATAGTGAGCCGTTCTCCAACCCTTTGGCCCCCGATGGCCACGATGTGGATGATCCT |
| CACTCCTTCCACCAATCAAAACTCACCAATGAAGACTTCAGGAAANTNNTCATGACCCCC |
| AGGGNTGCACNTACNTNTGCACCACNTTNTAANTNNNNTCACCATGAGATGCCAAGGGAG |
| TACAATGAGGATGAAGACCCAGCTGCACGAAGGAGGAAAAAGAAAAGTTATTATGCCAAG |
| CTACGCCAACAAGAAATTGAGAGAGAGAGAGCTAGCAGAGAAGTACCGGGATCGTGCC |
| AAGGAACGGAGAGATGGAGTGAACAAAGATTATGAAGAAACCGAGCTTATCAGCACCACA |
| GCTAACTATAGGGCTGTTGGCCCCACTGCTGAGGCGGACAAATCAGCTRCAGNNRAGAGA |
| AGACANWNDAHCNAGGAGTCCAAATTCTTGGGTGGTGACATGGAACACACCCATTTGGTG |
| AAAGGCTTGGATTTTGNTNTGCTTCHNAANGTNCGAGCTGAGATTGNCMSCMNANARAAA |
| NARGAARANGNNCTGATGGNAAANCCCCMGAAAGAAACCAAGAAAGATGAGGATCCTGAA |
| AATAAAATTGAATTTAAAACACGTCTGGGCCGCAATGTTTACCGAATGCTTTTTAAGAGC |
| AAAGCATATGAGCGGAATGAGTTGTTCCTGCCGGGCCGCATGGCCTATGTGGTAGACCTG |
| GATGATGAGTATGCTGACACAGATATCCCCACCACTCTTATCCCGCAGCAAGGCTGATTG |
| CCCCACCATGGAGGCCCAGACCACACTGACCACAAATGACATTGTCATTAGCAAGCTGAC |
| CCAGATCCTTTCATACCTGAGGCAGGGAACCCGTAACAAGAAGCTTAAGAAGAAGGATAA |
| AGGGAAGCCGGAAGAGAAGAAACCTCCTGAGGCTGACATGAATATTTTTGAAGACATTGG |
| GGATTACGTACCCTCCACAACCAAGACACCTCGGGACAAGGAGCGGGAGAGATATCGGGA |
| ACGGGAGCGTGATCGGGAAAGAGACAGAGACCGTGACCGAGAGCGAGAGCGAGAACGAGA |
| TCGGGAACGAGAGCGAGAGCGGGACCGAGAGAGAGAAGAGGAAAAGAAGAGACACAGCTA |
| CTTTGAGAAGCCAAAAGTAGATGATGAGCCCATGGACGTTGACAAAGGACCTGGGTCTAC |
| CAAGGAGTTGATCAAGTCCATCAATGAAAAGTTTGCTGGGTCTGCTGGCTGGGAAGGCAC |
| AGAATCGCTGAAGAAGCCAGAAGACAAAAAGCAGCTGGGAGATTTCTTTGGCATGTCCAA |
| CAGTTATGCAGAGTGCTACCCAGCCACGATGGATGACATGGCTGTGGATAGTGATGAGGA |
| GGTGGATTATAGCAAAATGGACCAGGGTAACAAGAAGGGGCCCTTAGGCCGTTGGGACTT |
| TGATACCCAGGAAGAATACAGCGAGTATATGAACAACAAAGAAGCTTTGCCCAAGGCTGC |
| ATTCCAGTATGGTATCAAAATGTCTGAAGGGCGGAAAACCAGGCGCTTCAAGGAAACCAA |
| TGACAAAGCAGAGCTTGATCGCCAGTGGAAGAAGATTAGTGCAATCATTGANGAAGAGGA |
| AGAAGATGGAAGCTGATGGGGTTGAAGTCAAAAGACCAAAATACTAATCACTAGTTACAA |
| CCAGAGATGCTCCACAAGGATATGCTCCCCACTGTTTTCTTTCTACAATTTCCAAAGGTT |

TABLE 5-continued

CAA-1 cDNA

GCAAGATGTTTTTTTGTGATGAATATAAAATTTTATTGTGTAATTACTTGGTTCCATTAA

AATTGGTTAACTTGCTAAAAAAAAAA

TABLE 6

CAA-1 Coding Sequence

ATGATGAGTATGCTGACACAGATATCCCCACCACTCTTATCCCGCAGCAAGGCTGATTGC (SEQ ID NO:6)
CCCACCATGGAGGCCCAGACCACACTGACCACAAATGACATTGTCATTAGCAAGCTGACC
CAGATCCTTTCATACCTGAGGCAGGGAACCCGTAACAAGAAGCTTAAGAAGAAGGATAAA
GGGAAGCCGGAAGAGAAGAAACCTCCTGAGGCTGACATGAATATTTTTGAAGACATTGGG
GATTACGTACCCTCCACAACCAAGACACCTCGGGACAAGGAGCGGGAGAGATATCGGGAA
CGGGAGCGTGATCGGGAAAGAGACAGAGACCGTGACCGAGAGCGAGAGCGAGAACGAGAT
CGGGAACGAGAGCGAGAGCGGGACCGAGAGAGAGAAGAGGAAAAGAAGAGACACAGCTAC
TTTGAGAAGCCAAAAGTAGATGATGAGCCCATGGACGTTGACAAAGGACCTGGGTCTACC
AAGGAGTTGATCAAGTCCATCAATGAAAAGTTTGCTGGGTCTGCTGGCTGGGAAGGCACA
GAATCGCTGAAGAAGCCAGAAGACAAAAAGCAGCTGGGAGATTTCTTTGGCATGTCCAAC
AGTTATGCAGAGTGCTACCCAGCCACGATGGATGACATGGCTGTGGATAGTGATGAGGAG
GTGGATTATAGCAAAATGGACCAGGGTAACAAGAAGGGGCCCTTAGGCCGTTGGGACTTT
GATACCCAGGAAGAATACAGCGAGTATATGAACAACAAAGAAGCTTTGCCCAAGGCTGCA
TTCCAGTATGGTATCAAAATGTCTGAAGGGCGGAAAACCAGGCGCTTCAAGGAAACCAAT
GACAAAGCAGAGCTTGATCGCCAGTGGAAGAAGATTAGTGCAATCATTGAGAAGAGGAA
GAAGATGGAAGCTGA

TABLE 7

CAA-1 Amino Acid Sequence

Met Met Ser Met Leu Thr Gln Ile Ser Pro Pro Leu Leu Ser Arg (SEQ ID NO:7)
Ser Lys Ala Asp Cys Pro Thr Met Glu Ala Gln Thr Thr Leu Thr
Thr Asn Asp Ile Val Ile Ser Lys Leu Thr Gln Ile Leu Ser Tyr
Leu Arg Gln Gly Thr Arg Asn Lys Lys Leu Lys Lys Lys Asp Lys
Gly Lys Pro Glu Glu Lys Pro Pro Glu Ala Asp Met Asn Ile
Phe Glu Asp Ile Gly Asp Tyr Val Pro Ser Thr Thr Lys Thr Pro
Arg Asp Lys Glu Arg Glu Arg Tyr Arg Glu Arg Glu Arg Asp Arg
Glu Arg Asp Arg Asp Arg Asp Arg Glu Arg Glu Arg Glu Arg Asp
Arg Glu Arg Glu Arg Glu Arg Asp Arg Glu Arg Glu Glu Lys
Lys Arg His Ser Tyr Phe Glu Lys Pro Lys Val Asp Asp Glu Pro
Met Asp Val Asp Lys Gly Pro Gly Ser Thr Lys Glu Leu Ile Lys
Ser Ile Asn Glu Lys Phe Ala Gly Ser Ala Gly Trp Glu Gly Thr
Glu Ser Leu Lys Lys Pro Glu Asp Lys Lys Gln Leu Gly Asp Phe
Phe Gly Met Ser Asn Ser Tyr Ala Glu Cys Tyr Pro Ala Thr Met

TABLE 7-continued

CAA-1 Amino Acid Sequence

Asp Asp Met Ala Val Asp Ser Asp Glu Glu Val Asp Tyr Ser Lys

Met Asp Gln Gly Asn Lys Lys Gly Pro Leu Gly Arg Trp Asp Phe

Asp Thr Gln Glu Glu Tyr Ser Glu Tyr Met Asn Asn Lys Glu Ala

Leu Pro Lys Ala Ala Phe Gln Tyr Gly Ile Lys Met Ser Glu Gly

Arg Lys Thr Arg Arg Phe Lys Glu Thr Asn Asp Lys Ala Glu Leu

Asp Arg Gln Trp Lys Lys Ile Ser Ala Ile Ile Xaa Glu Glu Glu

Glu Asp Gly Ser

The longest predicted open reading frame (ORF) is 942 bp. This ORF begins with the second in frame start codon, and is preceded by a shorter, 126 bp ORF. The predicted protein for the long ORF is 314 amino acids with a molecular weight of 37 kDa. The estimated message was 2.1 kb, but only 756 bp of sequence was reported, which was the largest clone isolated form their cDNA library.

Expression of CAA-1 has been detected with PCR in 4/5 normal cartilage specimens, 1/2 grade 0, 3/3 grade I, 3/4 grade II, and 5/5 grade III chondrosarcoma. Expression as not detected in colon, breast, renal cell, and gastric carcinoma and corresponding normal tissues; osteogenic and soft tissue sarcoma; and giant cell tumor.

CAA-1 functions to regulate an immune response. Regulation of an immune response, e.g., inflammation, is critical for normal synovial joint physiology and tumor surveillance. HLA class II antigens are necessary for antigen presentation to T cells, and interferon gamma has been shown to upregulate HLA class II expression in many different normal and tumor cells, including chondrocytes and synovial lining cells. In addition, chondrocytes have been shown to function as antigen presenting cells. CAA-1 functions as a cytokine which inhibits the interferon gamma induced upregulation of HLA class II antigens. Thus, chondrocytes express a gene which modulates its own ability, as well as cells in surrounding synovium, to function as antigen presenting cells. Treating a synovial joint with a CAA-1 polypeptide decreases the expression of HLA II antigens. Thus, a CAA-1 polypeptide can be administered locally to reduce pathological such as that associated with rheumatoid arthritis and other inflammatory arthropathies.

CAA-1 is also expressed in neoplastic cartilage. CAA-1 inhibits interferon gamma induced upregulation of HLA Class II. Expression of CAA-1 by tumor cells may be a mechanism of escape from immunorecognition, i.e. increased CAA-1 expression diminishes the ability of the host to control tumor growth through immunologic mechanisms. Treatment of chondrosarcoma by inhibiting the expression of CAA-1 or function of the CAA-1 gene product enhances the ability of the host immune system to control tumor growth through immunologic mechanisms.

EXAMPLE 2

Production and Purification of Recombinant CSA and CAA Polypeptides

To produce recombinant polypeptides, DNA encoding a CSA or CAA polypeptide in an appropriate expression vector is transfected into a cell. Standard methods for transfecting cells with isolated nucleic acid are well known to those skilled in the art of molecular biology. For example, prokaryotic or eukaryotic cells in culture can be transfected with the DNA of the invention operatively linked to expression control sequences appropriate for high-level expression in the cell. Such cells are useful for producing large amounts of the CSA-1 or CAA-1, which can be purified and used, e.g., as a therapeutic or for raising anti-CSA-1 or anti-CAA-1 antibodies.

For example, the recombinant gene product may be expressed as a fusion protein and purified using a commercially available expression and purification system, e.g., the pFLAG expression system (IBI). Recombinant polypeptides are injected into a rabbit or rodent to produce antibodies as described below.

EXAMPLE 3

Production of Antibodies Specific for CSA or CAA Polypeptides

Antibodies specific for CSA polypeptides can be obtained by techniques well known in the art. Such antibodies can be polyclonal or monoclonal. Polyclonal antibodies can be obtained, for example, by the methods described in Ghose et al., Methods in Enzymology, Vol. 93, 326–327, 1983. For example, a CSA-1 polypeptide (containing 23–24 amino acids, e.g., a polypeptide containing RRQTLSHGSSS-PARAC (SEQ ID NO:8) was used as an immunogen to stimulate the production of CSA-1-reactive polyclonal antibodies in the antisera of a rabbit. Similar methods can be used to raise antisera in animals such as goats, sheep, and rodents.

Monoclonal antibodies useful in the present invention can be obtained by the well known process described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for a CSA polypeptide. Preferably, the antibody will have an affinity of at least about $10^8$ liters/mole and more preferably, an affinity of at least about $10^9$ liters/mole. The use of such monoclonal antibodies provides a means of obtaining greater sensitivity in the assays of the present invention compared with the use of polyclonal antibodies.

EXAMPLE 4

Transgenic Animals

CSA polypeptides can also be expressed in transgenic animals. These animals represent a model system for the study of disorders that are caused by or exacerbated by overexpression or underexpression of a CSA polypeptide, and for the development of therapeutic agents that modulate the expression or activity of a CSA polypeptide.

A CSA-1 knockout animal is useful to study CSA-1 function. Immunostaining of mouse embryos with anti-CSA-1 antibody showed staining of the musculoskeletal precursor. A csa-1 transgene with a null mutation results in an animal which does not express the CSA-1 gene, a condition which may lead to developmental abnormalities since some genes expressed by tumors are also expressed during normal embryological development.

Alternatively, a transgenic animal overexpressing the CSA-1 is useful to study the development chondrosarcoma. Such an animal would be a useful tool for evaluating treatment of this tumor.

Transgenic animals can be farm animals (pigs, goats, sheep, cows, horses, rabbits, and the like) rodents (such as rats, guinea pigs, and mice), non-human primates (for example, baboons, monkeys, and chimpanzees), and domestic animals (for example, dogs and cats). Transgenic mice are especially preferred.

Any technique known in the art can be used to introduce a csa-1 transgene into animals to produce the founder lines of transgenic animals. Such techniques include, but are not limited to, pronuclear microinjection (U.S. Pat. No. 4,873, 191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983).

When it is desired that the csa-1 transgene be integrated into the chromosomal site of the endogenous csa-1 gene, gene targeting is preferred. Briefly, when such a technique is to be used, vectors containing some nucleotide sequences homologous to an endogenous csa-1 gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous csa-1 gene in only that cell type (Gu et al., *Science* 265:103, 1984). The regulatory sequences required for such a cell-type specific inactivation will depend upon the particular cell type of interest, and will be apparent to those of skill in the art. These techniques are useful for preparing "knock outs" having no functional csa or caa gene.

Once transgenic animals have been generated, the expression of the recombinant transgene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of csa or caa gene-expressing tissue can also be evaluated immunocytochemically using antibodies specific for the transgene product.

For a review of techniques that can be used to generate and assess transgenic animals, skilled artisans can consult Gordon (*Intl. Rev. Cytol.* 115:171–229, 1989), and may obtain additional guidance from, for example: Hogan et al. "Manipulating the Mouse Embryo" (Cold Spring Harbor Press, Cold Spring Harbor, N.Y., 1986; Krimpenfort et al., *Bio/Technology* 9:86, 1991; Palmiter et al., *Cell* 41:343, 1985; Kraemer et al., "Genetic Manipulation of the Early Mammalian Embryo," Cold Spring Harbor Press, Cold Spring Harbor, N.Y., 1985; Hammer et al., *Nature* 315:680, 1985; Purcel et al., *Science,* 244:1281, 1986; Wagner et al., U.S. Pat. No. 5,175,385; and Krimpenfort et al., U.S. Pat. No. 5,175,384.

EXAMPLE 5

Diagnosis of Chondrosarcoma

The invention includes a method of detecting cartilaginous neoplasms in a sample of patient-derived tissue. Detection of csa-1 expression (by measuring gene transcripts or gene products) in a patient sample compared to a control sample or CSA-1 polypeptide would predict chondrogenesis indicative of, e.g., chondrosarcoma. The diagnostic method of the invention is carried out by measuring csa gene expression in a tissue, e.g, a biopsy, or in a bodily fluid, e.g., blood or plasma. Detection of expression and determination of the level of gene expression is measured using methods known in the art, e.g., in situ hybridization, Northern blot analysis, or Western blot analysis using CSA-1-specific monoclonal or polyclonal antibodies. An increase in the level of csa-1 expression per cell in the test sample of tissue compared to the level per cell in control tissue indicates the presence of a chondrosarcoma in the test sample. For example, tissue obtained at an biopsy could be tested for CSA-1 expression, e.g., the level of CSA-1 transcript or polypeptide. An increased level of CSA-1 transcript or polypeptide (compared to normal tissue) indicates a high probability of chondrosarcoma. For example, PCR was used to detect expression csa-1 in 15 patient-derived chondrosarcoma biopsy samples. In contrast, no csa-1 expression was detected in 3 patient-derived normal control samples.

The methods described above can also be used to determine the grade of a tumor. Northern blotting and quantitative PCR techniques are used to determine the level of expression of csa gene expression. For example, elevated CSA-1 expression correlates with a higher grade of tumor.

The diagnostic procedures described above are useful to identify patients in need of therapeutic intervention to reduce or prevent chondrosarcoma.

EXAMPLE 6

Methods of Therapy

Patients with chondrosarcoma can be treated by administering CSA-1 antisense nucleic acids or ribozymes. Other malignant conditions, which are characterized by a increase in CSA-1 expression may be treated in a similar manner.

Antisense therapy is used to inhibit expression of proteins, e.g., CSA-1, involved in chondrogenesis, e.g., that associated with chondrosarcoma. For example, an antisense strand of csa-1 (either RNA or DNA) is directly introduced into the cells in a form that is capable of binding to the mRNA transcripts. Alternatively, a vector-containing sequence which, which once within the target cells is transcribed into the appropriate antisense mRNA, may be administered. Antisense nucleic acids which hybridize to mRNA can decrease or inhibit production of the polypeptide product encoded by a gene by associating with the normally single-stranded mRNA transcript, thereby interfering with translation and thus, expression of the protein.

Ribozyme therapy can also be used to inhibit gene expression. Ribozymes bind to specific mRNA and then cut it at a predetermined cleavage point, thereby destroying the transcript. These RNA molecules may be used to inhibit expression of a csa gene involved in chondrogenesis associated with chondrosarcoma according to methods known in the art (Sullivan et al., 1994, J. Invest. Derm. 103:85S–89S; Czubayko et al., 1994, J. Biol. Chem. 269:21358–21363; Mahieu et al, 1994, Blood 84:3758–65; Kobayashi et al. 1994, Cancer Res. 54:1271–1275).

Another therapeutic approach to inhibiting the expression of proteins or polypeptides is the production of intracellularly expressed antibodies which, when expressed in a cell, bind to and prevent the transport and surface expression of target proteins. Intracellular antibodies may be expressed in a cell using known techniques (Chen et al., 1994, Hum. Gene Ther. 5:595–601).

Gene therapy may be carried out by administering to a patient a nucleic acid encoding a therapeutic polypeptide, e.g., a tumor suppressor gene such as caa-1, by standard vectors and/or gene delivery systems. Suitable gene delivery systems may include liposomes, receptor-mediated delivery systems, naked DNA, and viral vectors such as herpes viruses, retroviruses, adenoviruses and adeno-associated viruses, among others.

As is discussed above, undesired or pathological inflammation such as that associated with rheumatoid arthritis and other inflammatory arthropathies can be treated by inhibiting CAA-1 expression. Antisense therapy and ribozyme therapy can be used to inhibit CAA-1 expression, and intracellular immunization using DNA encoding an anti-CAA-1 antibody can be used to inhibit function of the gene product.

A therapeutic composition may include one or more compounds, e.g., nucleic acids or immunosuppressive agents, and a pharmaceutically acceptable carrier. The therapeutic composition may also include a gene delivery system as described above. Pharmaceutically acceptable carriers are biologically compatible vehicles which are suitable for administration to an animal: e.g., physiological saline. A therapeutically effective amount of a compound is an amount which is capable of producing a medically desirable result in a treated animal, e.g., inhibition of expression of a target gene, e.g., a cell surface or secreted protein, or inhibition of cell activity, e.g., proliferation, migration, antigen presentation, antibody production, or cytokine production.

Parenteral administration, such as intravenous, subcutaneous, intramuscular, and intraperitoneal delivery routes, may be used to deliver the compound, with intravenous administration being the preferred route. Dosages for any one patient depends upon many factors, including the patient's size, body surface area, age, the particular compound to be administered, sex, time and route of administration, general health, and other drugs being administered concurrently. Dosages of the compound to be administered will vary (doses of immunosuppressive agents are expected to be in the range of doses used for administration of other immunosuppression agents known in the art). A preferred dosage for intravenous administration of nucleic acids is from approximately $10^6$ to $10^{22}$ copies of the nucleic acid molecule. Alternatively, the compound may be administered via a timed-release implant placed in close proximity to diseased tissue or a surgical site after removal of neoplastic tissue.

CSA polypeptides or CAA polypeptides, e.g., a CAA-1 polypeptide, may be administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 μmoles of the polypeptide of the invention would be administered per kg of body weight per day. The compositions of the invention are useful for parenteral administration, such as intravenous, subcutaneous, intramuscular, and intraperitoneal. Alternatively, a CAA polypeptide, e.g., CAA-1, can be administered as an implant for slow release at the site of an inflammatory lesion.

DNA (csa-1 encoding DNA, tumor cell-specific promoters, and vectors) of the invention may be introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others. For example, the DNA of the invention under the control of a strong constitutive promoter may be administered locally using an adenovirus delivery system.

The DNA of the invention may be administered in a pharmaceutically acceptable carrier. The therapeutic composition may also include a gene delivery system as described above. Pharmaceutically acceptable carriers are biologically compatible vehicles which are suitable for administration to an animal e.g., physiological saline. A therapeutically effective amount is an amount of the nucleic acid of the invention which is capable of producing a medically desirable result in a treated animal.

As is well known in the medical arts, dosage for any given patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule. Determination of optimal dosage is well within the abilities of a pharmacologist of ordinary skill. Drugs which inhibit the CSA-1 promoter may also be administered as described above to decrease the level of expression CSA-1 in tissues.

EXAMPLE 7

Identification of Compounds that Decrease csa or caa Gene Expression

A method of screening candidate compounds to identify compounds capable of inhibiting csa gene, e.g. csa-1, expression includes the following steps: providing a chondrosarcoma cell; contacting the cell with a candidate compound; and determining the amount of csa-1 expression in the cell, e.g., by immunostaining to detect a CSA-1 polypeptide or in situ hybridization, PCR, or Northern blotting to detect csa-1 transcripts. A decrease in the amount of csa-1 expression in cells exposed to the candidate compound compared to the amount of expression in cells in the absence of compound indicates that the compound inhibits expression of csa-1 in chondrosarcoma cells.

Compounds that inhibit csa-1 expression can also be identified by contacting the csa-1 promoter linked to a reporter gene with a candidate compound and measuring the level of expression of the reporter gene in the presence and absence of the compound. An decreased level of expression in the presence of the compound compared to that in its presence indicates that the compound inhibits expression of csa-1.

The screening methods described above can also be used to identify compounds which inhibit expression of a caa gene such as caa-1.

Other embodiments are within the following claims.

What is claimed is:

```
                              SEQUENCE LISTING

<160> NUMBER OF SEQ ID NOS: 8

<210> SEQ ID NO 1
<211> LENGTH: 164
<212> TYPE: DNA
<213> ORGANISM: Homo sapiens
<220> FEATURE:
<221> NAME/KEY: CDS
<222> LOCATION: (1)...(156)

<400> SEQUENCE: 1 atg gct gcg ggt ccc agg cca gga gct ccc tgc agg gcg ggg gct ccc        48
Met Ala Ala Gly Pro Arg Pro Gly Ala Pro Cys Arg Ala Gly Ala Pro
  1               5                  10                  15 acg atc gta ttg acc tct gga aga aga cag aca ctt tcc cac ggg agc        96
Thr Ile Val Leu Thr Ser Gly Arg Arg Gln Thr Leu Ser His Gly Ser
                 20                  25                  30 tcc tct cca gcc aga gct aca ctt ggc aaa cct ttg gtc cta aat gat       144
Ser Ser Pro Ala Arg Ala Thr Leu Gly Lys Pro Leu Val Leu Asn Asp
             35                  40                  45 tat tca ctg aat tgaagaaa                                              164
Tyr Ser Leu Asn
     50

<210> SEQ ID NO 2
<211> LENGTH: 52
<212> TYPE: PRT
<213> ORGANISM: Homo sapiens

<400> SEQUENCE: 2

Met Ala Ala Gly Pro Arg Pro Gly Ala Pro Cys Arg Ala Gly Ala Pro
  1               5                  10                  15

Thr Ile Val Leu Thr Ser Gly Arg Arg Gln Thr Leu Ser His Gly Ser
                 20                  25                  30

Ser Ser Pro Ala Arg Ala Thr Leu Gly Lys Pro Leu Val Leu Asn Asp
             35                  40                  45

Tyr Ser Leu Asn
     50

<210> SEQ ID NO 3
<211> LENGTH: 884
<212> TYPE: DNA
<213> ORGANISM: Homo sapiens

<400> SEQUENCE: 3
acttccctgg gttcacagca ggggtggaac tggattcttc ctggatgggg atccagatgg      60
aggtggagct gcaccccttg tagagaatgg ctgcgggtcc caggccagga gctccctgca     120 gggcggggc tcccacgatc gtattgacct ctggaagaag acagacactt tcccacggga     180
gctcctctcc agccagagct acacttggca aacctttggt cctaaatgat tattcactga     240
attgaagaaa tacggtttac atatcttcca agtatatatg tagggttgat ttgggaagca     300
gaacacagca gcccaaattt gcttgtaatg tctgcgacta cagcctgctg gcctgccttc     360
actgtcttgg gggaagctcg gggagaccag gtggactgga gtagactgtg cagagacact     420
ggtctggtga agatgtccag gaaaccacga gcctccagcc cattttccaa caaccaccca     480
```

-continued

```
tcaacaccaa agaggttccc aagacaaccc agaagggaaa agggacccgt caaggaagtt       540
ccaggaacaa aaggctctcc ctaaaagacc accgcttcaa aaaaacctga ggaatggagt       600
gggccaacac tatccagcca ctctgaccag ccgaacgagg aactcaatca aaatgcgcca       660
tagcaggacc acaagggcaa ggagaccacc gccttctcca gtgcttcctt gggcagccag       720
taattcccag gcaaggccag agacttcaag tctatctgaa aagtctccag aagtctaacc       780
ccagataaat agccaacagg gtgtagagta cgttttacac ccaaagggta atgccccatg       840
gtgatggaaa taaaatgaac atgttgtaaa atgaaaaaaa aaa                         884
```

<210> SEQ ID NO 4
<211> LENGTH: 14
<212> TYPE: DNA
<213> ORGANISM: Artificial Sequence
<220> FEATURE:
<223> OTHER INFORMATION: synthetically generated
<220> FEATURE:
<221> NAME/KEY: misc_feature
<222> LOCATION: (1)...(14)
<223> OTHER INFORMATION: n = A,T,C or G

<400> SEQUENCE: 4

```
tttttttttt ttvn                                                         14
```

<210> SEQ ID NO 5
<211> LENGTH: 1946
<212> TYPE: DNA
<213> ORGANISM: Homo sapiens
<220> FEATURE:
<221> NAME/KEY: misc_feature
<222> LOCATION: (1)...(1946)
<223> OTHER INFORMATION: n = A,T,C or G

<400> SEQUENCE: 5

```
cacgcaaagc agtgtgggtt gattctgagg tgcactgtgg aaagagcttt gtcgctgcgg       60
tgttgctgtt ggagactcga ttgttggtga cagcgaaaga acgataacaa aatgccggag       120
cgagatagtg agccgttctc caacccttg gcccccgatg ccacgatgt ggatgatcct       180 cactccttcc accaatcaaa actcaccaat gaagacttca ggaaantnnt catgaccccc       240
agggntgcac ntacntntgc accacnttnt aantnnnntc accatgagat gccaagggag       300
tacaatgagg atgaagaccc agctgcacga aggaggaaaa agaaaagtta ttatgccaag       360
ctacgccaac aagaaattga gagagagaga gagctagcag agaagtaccg ggatcgtgcc       420
aaggaacgga gagatggagt gaacaaagat tatgaagaaa ccgagcttat cagcaccaca       480
gctaactata gggctgttgg ccccactgct gaggcggaca aatcagctrc agnnragaga       540
agacanwnda hcnaggagtc caaattcttg ggtggtgaca tggaacacac ccatttggtg       600
aaaggcttgg attttgntnt gcttchnaan gtncgagctg agattgncms cmnanaraaa       660
nargaarang nnctgatggn aaancccmcg aaagaaacca agaaagatga ggatcctgaa       720
aataaaattg aatttaaaac acgtctgggc cgcaatgttt accgaatgct ttttaagagc       780
aaagcatatg agcggaatga gttgttcctg ccgggccgca tggcctatgt ggtagacctg       840
gatgatgagt atgctgacac agatatcccc accactctta tcccgcagca aggctgattg       900
ccccaccatg gaggcccaga ccacactgac cacaaatgac attgtcatta gcaagctgac       960
ccagatcctt tcatacctga ggcagggaac ccgtaacaag aagcttaaga agaaggtaaa       1020
agggaagccg gaagagaaga aacctcctga ggctgacatg aatatttttg aagacattgg      1080
```

-continued

```
ggattacgta ccctccacaa ccaagacacc tcgggacaag gagcgggaga gatatcggga      1140
acgggagcgt gatcgggaaa gagacagaga ccgtgaccga gagcgagagc gagaacgaga      1200
tcgggaacga gagcgagagc gggaccgaga gagagaagag gaaaagaaga gacacagcta      1260
ctttgagaag ccaaaagtag atgatgagcc catggacgtt gacaaaggac ctgggtctac      1320
caaggagttg atcaagtcca tcaatgaaaa gtttgctggg tctgctggct gggaaggcac      1380
agaatcgctg aagaagccag aagacaaaaa gcagctggga gatttctttg gcatgtccaa      1440
cagttatgca gagtgctacc cagccacgat ggatgacatg gctgtggata gtgatgagga      1500
ggtggattat agcaaaatgg accagggtaa caagaagggg cccttaggcc gttgggactt      1560
tgatacccag gaagaataca gcgagtatat gaacaacaaa gaagctttgc ccaaggctgc      1620
attccagtat ggtatcaaaa tgtctgaagg gcggaaaacc aggcgcttca aggaaaccaa      1680
tgacaaagca gagcttgatc gccagtggaa gaagattagt gcaatcattg angaagagga      1740
agaagatgga agctgatggg gttgaagtca aaagaccaaa atactaatca ctagttacaa      1800
ccagagatgc tccacaagga tatgctcccc actgttttct ttctacaatt tccaaaggtt      1860
gcaagatgtt tttttgtgat gaatataaaa ttttattgtg taattacttg gttccattaa      1920
aattggttaa cttgctaaaa aaaaaa                                           1946

<210> SEQ ID NO 6
<211> LENGTH: 915
<212> TYPE: DNA
<213> ORGANISM: Homo sapiens
<220> FEATURE:
<221> NAME/KEY: CDS
<222> LOCATION: (1)...(912)
<221> NAME/KEY: misc_feature
<222> LOCATION: (1)...(915)
<223> OTHER INFORMATION: n = A,T,C or G

<400> SEQUENCE: 6 atg atg agt atg ctg aca cag ata tcc cca cca ctc tta tcc cgc agc        48
Met Met Ser Met Leu Thr Gln Ile Ser Pro Pro Leu Leu Ser Arg Ser
  1               5                  10                  15 aag gct gat tgc ccc acc atg gag gcc cag acc aca ctg acc aca aat        96
Lys Ala Asp Cys Pro Thr Met Glu Ala Gln Thr Thr Leu Thr Thr Asn
             20                  25                  30 gac att gtc att agc aag ctg acc cag atc ctt tca tac ctg agg cag       144
Asp Ile Val Ile Ser Lys Leu Thr Gln Ile Leu Ser Tyr Leu Arg Gln
         35                  40                  45 gga acc cgt aac aag aag ctt aag aag aag gat aaa ggg aag ccg gaa       192
Gly Thr Arg Asn Lys Lys Leu Lys Lys Lys Asp Lys Gly Lys Pro Glu
     50                  55                  60 gag aag aaa cct cct gag gct gac atg aat att ttt gaa gac att ggg       240
Glu Lys Lys Pro Pro Glu Ala Asp Met Asn Ile Phe Glu Asp Ile Gly
 65                  70                  75                  80 gat tac gta ccc tcc aca acc aag aca cct cgg gac aag gag cgg gag       288
Asp Tyr Val Pro Ser Thr Thr Lys Thr Pro Arg Asp Lys Glu Arg Glu
                 85                  90                  95 aga tat cgg gaa cgg gag cgt gat cgg gaa aga gac aga gac cgt gac       336
Arg Tyr Arg Glu Arg Glu Arg Asp Arg Glu Arg Asp Arg Asp Arg Asp
            100                 105                 110 cga gag cga gag cga gaa cga gat cgg gaa cga gag cga gag cgg gac       384
Arg Glu Arg Glu Arg Glu Arg Asp Arg Glu Arg Glu Arg Glu Arg Asp
        115                 120                 125 cga gag aga gaa gag gaa aag aag aga cac agc tac ttt gag aag cca       432
Arg Glu Arg Glu Glu Glu Lys Lys Arg His Ser Tyr Phe Glu Lys Pro
    130                 135                 140
```

```
aaa gta gat gat gag ccc atg gac gtt gac aaa gga cct ggg tct acc    480
Lys Val Asp Asp Glu Pro Met Asp Val Asp Lys Gly Pro Gly Ser Thr
145                 150                 155                 160 aag gag ttg atc aag tcc atc aat gaa aag ttt gct ggg tct gct ggc    528
Lys Glu Leu Ile Lys Ser Ile Asn Glu Lys Phe Ala Gly Ser Ala Gly
                165                 170                 175 tgg gaa ggc aca gaa tcg ctg aag aag cca gaa gac aaa aag cag ctg    576
Trp Glu Gly Thr Glu Ser Leu Lys Lys Pro Glu Asp Lys Lys Gln Leu
            180                 185                 190 gga gat ttc ttt ggc atg tcc aac agt tat gca gag tgc tac cca gcc    624
Gly Asp Phe Phe Gly Met Ser Asn Ser Tyr Ala Glu Cys Tyr Pro Ala
        195                 200                 205 acg atg gat gac atg gct gtg gat agt gat gag gag gtg gat tat agc    672
Thr Met Asp Asp Met Ala Val Asp Ser Asp Glu Glu Val Asp Tyr Ser
    210                 215                 220 aaa atg gac cag ggt aac aag aag ggg ccc tta ggc cgt tgg gac ttt    720
Lys Met Asp Gln Gly Asn Lys Lys Gly Pro Leu Gly Arg Trp Asp Phe
225                 230                 235                 240 gat acc cag gaa gaa tac agc gag tat atg aac aac aaa gaa gct ttg    768
Asp Thr Gln Glu Glu Tyr Ser Glu Tyr Met Asn Asn Lys Glu Ala Leu
                245                 250                 255 ccc aag gct gca ttc cag tat ggt atc aaa atg tct gaa ggg cgg aaa    816
Pro Lys Ala Ala Phe Gln Tyr Gly Ile Lys Met Ser Glu Gly Arg Lys
            260                 265                 270 acc agg cgc ttc aag gaa acc aat gac aaa gca gag ctt gat cgc cag    864
Thr Arg Arg Phe Lys Glu Thr Asn Asp Lys Ala Glu Leu Asp Arg Gln
        275                 280                 285 tgg aag aag att agt gca atc att gan gaa gag gaa gaa gat gga agc    912
Trp Lys Lys Ile Ser Ala Ile Ile Xaa Glu Glu Glu Glu Asp Gly Ser
    290                 295                 300 tga                                                                 915
```

<210> SEQ ID NO 7
<211> LENGTH: 304
<212> TYPE: PRT
<213> ORGANISM: Homo sapiens
<220> FEATURE:
<221> NAME/KEY: VARIANT
<222> LOCATION: (1)...(304)
<223> OTHER INFORMATION: Xaa = Any Amino Acid

<400> SEQUENCE: 7

```
Met Met Ser Met Leu Thr Gln Ile Ser Pro Pro Leu Leu Ser Arg Ser
1               5                   10                  15

Lys Ala Asp Cys Pro Thr Met Glu Ala Gln Thr Thr Leu Thr Thr Asn
                20                  25                  30

Asp Ile Val Ile Ser Lys Leu Thr Gln Ile Leu Ser Tyr Leu Arg Gln
            35                  40                  45

Gly Thr Arg Asn Lys Lys Leu Lys Lys Asp Lys Gly Lys Pro Glu
        50                  55                  60

Glu Lys Lys Pro Pro Glu Ala Asp Met Asn Ile Phe Glu Asp Ile Gly
65                  70                  75                  80

Asp Tyr Val Pro Ser Thr Thr Lys Thr Pro Arg Asp Lys Glu Arg Glu
                85                  90                  95

Arg Tyr Arg Glu Arg Glu Arg Asp Arg Glu Arg Asp Arg Asp Arg Asp
            100                 105                 110

Arg Glu Arg Glu Arg Glu Arg Asp Arg Glu Arg Glu Arg Glu Arg Asp
        115                 120                 125
```

-continued

```
Arg Glu Arg Glu Glu Lys Lys Arg His Ser Tyr Phe Glu Lys Pro
    130                 135                 140

Lys Val Asp Asp Glu Pro Met Asp Val Asp Lys Gly Pro Gly Ser Thr
145                 150                 155                 160

Lys Glu Leu Ile Lys Ser Ile Asn Glu Lys Phe Ala Gly Ser Ala Gly
                165                 170                 175

Trp Glu Gly Thr Glu Ser Leu Lys Lys Pro Glu Asp Lys Lys Gln Leu
            180                 185                 190

Gly Asp Phe Phe Gly Met Ser Asn Ser Tyr Ala Glu Cys Tyr Pro Ala
        195                 200                 205

Thr Met Asp Asp Met Ala Val Asp Ser Asp Glu Glu Val Asp Tyr Ser
    210                 215                 220

Lys Met Asp Gln Gly Asn Lys Lys Gly Pro Leu Gly Arg Trp Asp Phe
225                 230                 235                 240

Asp Thr Gln Glu Glu Tyr Ser Glu Tyr Met Asn Asn Lys Glu Ala Leu
                245                 250                 255

Pro Lys Ala Ala Phe Gln Tyr Gly Ile Lys Met Ser Glu Gly Arg Lys
            260                 265                 270

Thr Arg Arg Phe Lys Glu Thr Asn Asp Lys Ala Glu Leu Asp Arg Gln
        275                 280                 285

Trp Lys Lys Ile Ser Ala Ile Ile Xaa Glu Glu Glu Glu Asp Gly Ser
    290                 295                 300

<210> SEQ ID NO 8
<211> LENGTH: 16
<212> TYPE: PRT
<213> ORGANISM: Homo sapiens

<400> SEQUENCE: 8

Arg Arg Gln Thr Leu Ser His Gly Ser Ser Ser Pro Ala Arg Ala Cys
1               5                   10                  15
```

1. An isolated nucleic acid molecule encoding a chondrosarcoma associated (CSA) polypeptide, wherein said nucleic acid molecule comprises the nucleotide sequence of SEQ ID NO:1.

2. An isolated nucleic acid molecule encoding a chondrosarcoma associated (CSA) polypeptide, wherein said nucleic acid molecule comprises a nucleotide sequence encoding a polypeptide sequence which polypeptide sequence is identical to at least 50 amino acids of the sequence of SEQ ID NO:2.

3. The nucleic acid molecule of claim 1 or 2, wherein said nucleic acid molecule is operably linked to nucleic acid molecule comprising regulatory sequences for expression of said polypeptide, said regulatory sequences comprising a promoter.

4. A isolated cell comprising the nucleic acid molecule of claim 1 or 2.

5. A method of making a CSA polypeptide, comprising (a) providing the cell of claim 4, and (b) culturing it under conditions permitting expression of said nucleic acid molecule thereby making a CSA polypeptide.

6. An isolated nucleic acid molecule encoding a chondrosarcoma associated (CSA) polypeptide, wherein said nucleic acid molecule comprises a nucleotide sequence encoding a polypeptide comprising the sequence of SEQ ID NO:2.

7. An isolated nucleic acid molecule encoding a chondrosarcoma associated (CSA) polypeptide, wherein said nucleic acid molecule consists of: the nucleotide sequence of SEQ ID NO:1 or a degenerate variant thereof, wherein said variant encodes a polypeptide consisting of the sequence of SEQ ID NO:2.

* * * * *